United States Patent [19]
Kreiser et al.

[11] Patent Number: 5,856,199
[45] Date of Patent: Jan. 5, 1999

[54] COLORIMETRIC DRY REAGENT TEST DEVICE AND METHOD FOR THE DETERMINATION OF ANALYTES IN SOLUTIONS CONTAINING INTERFERING COLORED SUBSTANCES

[75] Inventors: Thomas Harry Kreiser, Elkhart; Eugenia Makowski, South Bend, both of Ind.

[73] Assignee: Environmental Test Systems, Inc., Elkhart, Ind.

[21] Appl. No.: 811,493

[22] Filed: Mar. 5, 1997

[51] Int. Cl.⁶ .......................... G01N 33/48; G01N 21/77

[52] U.S. Cl. .............................. 436/169; 436/164; 422/56

[58] Field of Search .................................. 422/56, 58, 6, 422/131, 127; 436/164, 169, 86

[56] References Cited

U.S. PATENT DOCUMENTS

| | | | |
|---|---|---|---|
| 3,973,909 | 8/1976 | Van Der Werf et al. | 422/55 |
| 5,424,215 | 6/1995 | Albarella et al. | 436/86 |
| 5,593,895 | 1/1997 | Cahill et al. | 436/86 |

*Primary Examiner*—Lyle A. Alexander
*Attorney, Agent, or Firm*—Zarley, McKee, Thomte, Voorhees & Sease

[57] ABSTRACT

A dry reagent colorimetric test system for determining analytes in sample solutions containing interfering colored materials is presented comprising a reagent impregnated matrix containing a chromogenic material responsive to the analyte being detected and a masking dyestuff for obviating the interference caused by the colored materials thus allowing a proportional visual estimation of the response of the chromogenic material due to the amount of analyte in the sample solution.

17 Claims, 2 Drawing Sheets

COLORIMETRIC DRY REAGENT TEST DEVICE AND METHOD FOR THE DETERMINATION OF ANALYTES IN SOLUTIONS CONTAINING INTERFERING COLORED SUBSTANCES

FIELD OF THE INVENTION

The present invention relates to improved calorimetric dry reagent test devices and methods for using such devices. More specifically, it relates to a system for overcoming or obviating interference caused by extraneous colored materials or substances present in sample solutions.

BACKGROUND OF THE INVENTION

Dry reagent test devices using compositions containing chromogenic indicator materials incorporated in porous or absorbent matrices have become the systems of choice to determine the amount of various analytes in aqueous fluids. Even though such test devices excel for use in field or on-site testing situations, they can likewise be advantageously used in laboratory settings. Such systems, commonly called reagent strips or "dip-and-read" test devices, can be made to give semi-quantitative and to some extent quantitative results when the user understands the limitations of the test methodology and the sample makeup. One serious problem commonly encountered by test strip developers and users is the presence of interfering colored components or materials in the test sample fluid or solution. These interfering colored components may be the result of the introduction of extraneous substances, such as naturally occurring colored materials often found in samples of ground water, or may be the result of the purposeful addition of dyestuffs to identify or delineate the particular fluid being analyzed, such as in the identification of a particular type of coolant fluid used in association with internal combustion engines.

SUMMARY OF THE INVENTION

The present invention involves a dry reagent impregnated matrix containing chromogenic indicator materials, which upon contact with an analyte in a highly colored test fluid, gives a discernible chromogenic response despite color interference caused by the coloration of the test fluid sample itself. More specifically, it has unexpectedly been found that in a calorimetric analytical procedure using chromogenic indicator materials, interferences caused by highly colored substances in a test sample can be obviated by including in the test reagent composition or matrix a masking dyestuff which combines with and allows the chromogenic material to generate a visually discernible color response which is indicative of the amount of analyte present in the test sample fluid despite the presence of such interfering colored material. In this regard, it was first found that by adding a masking dyestuff which has the same or substantially the same color characteristics as the interfering color, particularly pervasive interfering colors, such as red, can be obviated. The successful utilization of a dyestuff having essentially the same color characteristics as the interfering material was quite unexpected since it would, as a first reaction, appear to be inappropriate to add more interfering colored materials to the test composition as opposed to the more usual procedures in analytical chemistry which call for removal of the interfering substance by filtration or adsorption techniques.

Moreover, it was also unexpectedly found that in other instances involving situations in which the interfering colored materials in the test samples vary over a range of colors, such as from blue to red, by adding a masking dyestuff having red spectral color characteristics, a universal test device and method can be advantageously achieved.

Although the present invention has broad applicability in various fields of chemical analysis, it has been found to be especially useful in the determination of various analytes found in vehicular fluids such as, for example, coolant and brake fluids. These liquids usually are formulated to contain substantial amounts of identifying dyestuff to prevent intermingling of incompatible fluids in the same vehicle.

In this regard, the newer long life radiator coolants are commonly formulated to contain relatively large amounts of identifying red or blue dyestuffs which severely interfere with the calorimetric determination of analytes in such fluids. A particularly troublesome assay comprises the calorimetric determination of ethylene or propylene glycol, which ingredients are used to adjust the freezepoint of such fluids. Accordingly, a universal assay or test system to determine the freezepoint constituents of longlife coolants containing various identifying dyestuffs or highly colored components would be particularly utilitarian.

DESCRIPTION OF THE PRIOR ART

In the formulation of reagent test compositions for incorporation into an absorbent matrix test device, it has been common practice to include background dyestuffs in the test reagent composition to enhance or modify the color change of the primary chromogen. The following patents represent this line of thinking:

1. U.S. Pat. No. 3,092,465 to Adams et al. discloses as a casual afterthought the use of an inert dye to give the test composition a "uniform color background". See Col. 6, Line 18.
2. U.S. Pat. No. 3,438,737 to Atkinson et al. discloses and claims a protein test composition and device which uses a "background dye" to mostly control the color response of the indicator material due to the buffering action of the test system and the pH response range of the indicator. See Col. 4, lines 62–75 and Col. 5, lines 1–62.
3. U.S. Pat. No. 3,814,668 to Blake et al., discloses and claims a test composition for determining glucose in urine samples, which composition contains an iodide as a primary chromogen and a blue dye as a background color to give a gradient color response of from blue to brown to the presence of glucose in the sample. See Column 3, lines 41 to 56.

For background information relating to assays for automotive fluids and particularly radiator coolants, U.S. Pat. No. 3,973,909 to Van der Werf et al., discloses and claims a method for the determination of the freezepoint of automobile coolant (ethylene and propylene glycol) using a pH type indicator and a buffering agent.

Finally, the book entitled, "Light and Color in Nature and Art" by Williamson et al., John Wiley & Sons, New York, 1983, is an excellent background on the science and measurement of color.

BRIEF DESCRIPTION OF THE ACCOMPANYING DRAWINGS

DESCRIPTION OF THE PREFERRED EMBODIMENTS

Figure 1:
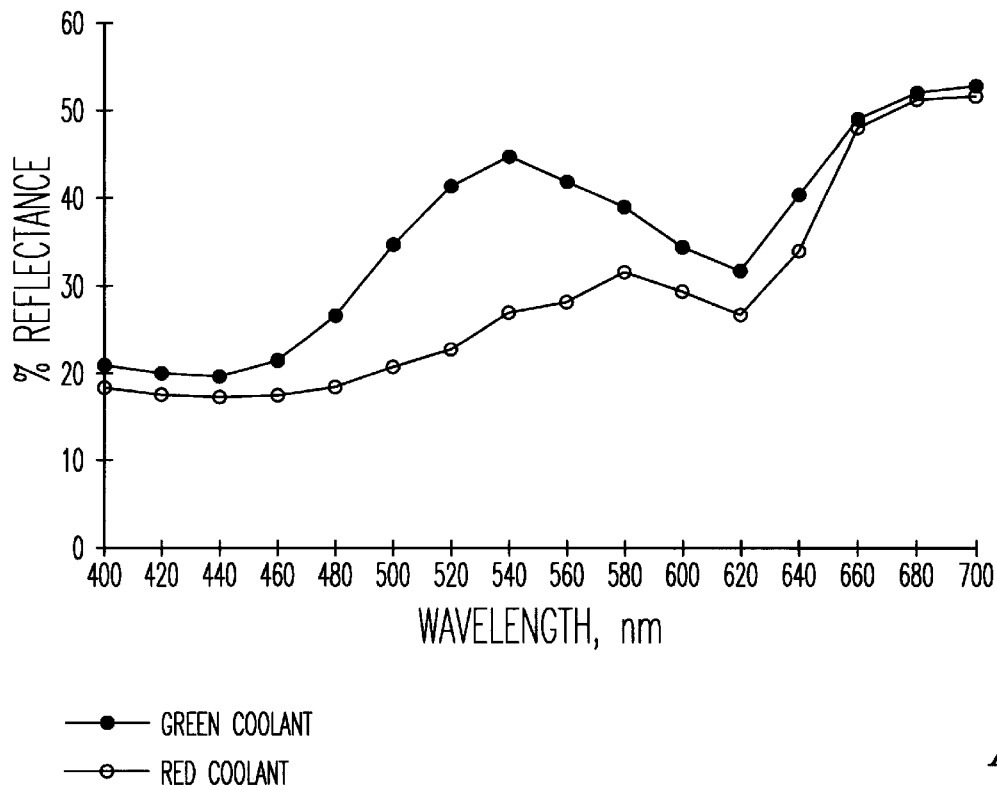
FIG. 1 is a graph showing spectral percent reflectance curves representing the results of Example 1 wherein red and green colored coolants are tested for the presence and amount of ethylene glycol using a standard tetrabromophenol blue indicator material reagent system.

As used herein the following definitions of terms apply: an "analyte" is a chemical, biochemical or fluid parameter being determined or assessed relative to a test sample fluid; a "calorimetric" analytical procedure is one in which an indicator is used to react as specifically as possible with the analyte to give a visual or otherwise detectable or discernible color response proportional to the amount or degree of analyte in the test fluid; a "chromogen" is a chemical compound which, in a chemical reaction with the analyte, is converted to a colored substance or dyestuff; a "color characteristic" is the means of measuring, identifying or describing a particular visually perceived color of an object or surface, either reflected or transmitted, using a name or a numerical value (described more fully hereinafter); "interfering colored substance" is the color appearance of the liquid being tested, such color either being naturally present in the fluid or added thereto as a mechanism for identifying the liquid being tested from other similar liquids; the "chromaticity" of a color is defined as the quality of the color as determined by its dominant wavelength and its purity; and, "masking dyestuff" is defined as a colored material or substance, added to the matrix or test composition by the test system formulator, such material having color characteristics which when combined or mixed with the reacted chromogen gives a resulting color which can be visually read in proportion to the amount of analyte present despite the presence of the interfering colored material present in the test sample.

The calorimetric test compositions, devices and methods of the present invention commonly employ reagent mixtures which give a visual color change upon contact with the analyte being determined. As used herein, the term "color change" means not only a change from one color to another but includes a change in the intensity or saturation of a color upon contact with an increased amount of analyte present in the fluid being tested. Such compositions or reagent systems invariably employ as a primary ingredient a chromogenic material specifically reactable with the analyte being determined. In addition to the chromogenic material, these test compositions commonly include numerous other active ingredients or excipients, such as buffers, catalysts, color stabilizers and enhancers, as well as inert ingredients such as thickeners, drying agents and surfactants which are used to assist in the formulation, processing and use of the test device.

In preparing the calorimetric compositions and devices of the present invention for commercial use, it has been found to be particularly advantageous and utilitarian to incorporate or impregnate the test composition into or onto a flat matrix which can be used to house or store the reagent composition and present the same to the test fluid as well as a means to allow the reaction to proceed and to compare the color developed to a standardized color chart for quantifying the amount of analyte present in the test fluid. A preferable and simple matrix material comprises a high quality, absorbent filter paper having a consistent and uniform density. This material serves to absorb a fixed amount of sample fluid which in turn increases the quantitation potential for the test device. In addition to paper, other matrix materials can comprise synthetic woven and non-woven fibrous materials, porous polymeric films, gels, and so forth. The impregnated matrix materials are usually cut into small rectangular areas or pads, of suitable size for visual examination, and attached to plastic or other stiffer support materials for ease of use and presentation to the sample fluid.

The reagent strip test devices of the present invention are usually used in combination with a standardized color chart to give a quantitative or semi-quantitative result which can then immediately be used by the analyst in accordance with a result oriented action plan. Standardized color charts are prepared by using known concentrations of analyte in a series of liquid samples and either instrumentally reading and duplicating the colors obtained or visually matching such colors to standard color books.

The novel component of the device and method of the present invention is the inclusion or use of one or more masking dyestuffs which materials obviate the color interference due to extraneous coloration of the sample fluid. Basically, these masking dyestuffs have color characteristics which, when combined with the interfering colored materials and the color response due to the normal color change of the chromogen in the test composition, modify or change the total color response of the test system into an area of the visual spectrum which allows a visual estimation of the reaction of the analyte with the chromogenic indicator despite the presence of large amounts of interfering color contributed by the test sample fluid.

Color, as perceived by the human eye, is a complex psychophysical phenomenon involving numerous scientific considerations. Such complex theories and laws are, to a large extent, beyond the scope of the present specification and need not be considered here; however, for the purpose of adequately defining, describing and attempting to understand the scope and parameters of the present invention, the color characteristics of 1) the chromogen (both before and after reacting with the analyte), 2) the interfering color, 3) the masking dyestuff, and 4) mixtures thereof, should be amenable to being measured and quantified in terms of light being reflected off of or through a source and received by a receptor in the form of instrumentation or the human eye. In other words, the term color, as used herein, is defined either using a descriptive name, such as red or blue, or as a spectral curve wherein wavelength of light is plotted against a power parameter.

As indicated above, over the years numerous methods have been developed to describe and measure light. The simplest, of course, involves the use of names to describe the color under scrutiny. Such name descriptions, without a corresponding dictionary and color samples, are usually quite inexact. A more precise method involves scanning a liquid or surface and plotting power against wavelength to develop diagrams which are commonly called spectral power distribution curves or SPDs.

One method of measuring color, utilized extensively in the field of analytical chemistry, commonly employs instrumentation called colorimeters or spectrophotometers which determine the color characteristics of a sample fluid by passing a light source having varying known characteristics (incident light) through the sample and measuring the light which emerges from the sample (transmitted light). By doing this, a curve can be developed which basically describes the color of the sample fluid. If absorbance is plotted against wavelength of light, a diagram is developed which is known as a spectral absorbance curve and the peak of the curve identifies the color of the sample fluid. For example, a red dyestuff will typically have a peak at about 500 nanometers.

A more restricted means or method of describing color as it relates to reflected light involves the use of spectral reflectance curves or SRCs. These diagrams display percent reflectance (%R) vs wavelength in nanometers (nm) of light reflected from a surface color. The incident light source in such curves is usually white.

A still more scientific or sophisticated way to measure color has been developed earlier in the century by an international group known as the Commission Internationale d'Eclairage or C.I.E.. The system devised by this group of scientists is known as the C.I.E. Chromaticity Diagram and basically measures three color qualities—luminance, dominant wavelength and purity, the latter two qualities combined known as chromaticity. The result is a complex diagram which can be used to give an accurate measure of a particular color.

Of the methods of measuring color described above, "spectral reflectance curves" (SRCs) and values based on such curves will be used to measure and evaluate the effectiveness of the test systems of the present invention and "spectral absorbance curves" (SACs) will be used to describe the color characteristics of certain components of the test systems, such as the masking dyestuffs. The rationale for this is that the devices and methods of the present invention were developed using visual reflectance estimations based on color charts and the dyestuffs used therein are commonly described in terms of absorbed light.

Accordingly, using SAC diagrams to define and describe color, it has been found that the masking dyestuffs of the present invention should advantageously have color characteristics which are capable of modifying or changing the SRC of the total color developed in the matrix by the reacted chromogen with the analyte in the presence of the interfering colored material so that the test sample color contribution is obviated or negated.

In this regard, it has unexpectedly been found that when a red interfering coloration is present in the test sample fluid and the chromogenic response of the test reagent is from yellow to blue, the addition of a red masking dyestuff, which has an SAC which peaks at from about 450 to 600 nanometers and preferably at about 500 nanometers, to the test composition obviates test sample color contribution. Moreover, it has also unexpectedly been found that the use of such a red dyestuff results in a test device that can also be used when the interfering colors in the test sample fluid are other than red. In other words, the resulting test device and method can be used to measure analytes when a wide range of interfering colors are present in the test fluid.

The masking dyestuffs used in the present invention are pigments or dyes commercially available for various applications and uses. Generally speaking, the selection of such materials depends on the color of the interfering material as well as the color generated by the chromogenic indicator materials when responding to the presence of the analyte. As previously stated, the masking dyestuff should have color characteristics which, when combined with the colors generated by the chromogenic indicator as well as the interfering colored materials in the sample fluid, result in a color which can be visually perceived to be proportional to the amount of analyte present in the sample fluid.

Since the amount of interfering colored materials encountered in using the test devices of the present invention can vary over a wide range of values, the concentration of masking dyestuff used in the compositions of the present invention must of necessity be defined functionally. Accordingly, the amount or concentration of masking dyestuff used in the test devices of the present invention is that which is necessary to mask the maximum amount of interfering colored materials absorbed into the test matrix upon immersion of the test device into the sample solution and still allow the estimation of the color response due to the reaction of the chromogenic materials with the analyte present in the sample fluid. Moreover, this color response or differentiation must be capable of being visually estimated over the range of concentrations encountered in the particular assay under consideration. In other words, the amount or concentration of masking dyestuff present in the test device must be sufficient to obviate or suppress any amount of interference due to the presence of colored interfering materials present in the fluid being tested and still allow a visual estimation of the color response of the reaction of the chromogen with the analyte present in the fluid being tested.

In the case of the determination of ethylene and propylene glycol in longlife radiator coolant using tetrabromophenol blue as the chromogenic material, the amount of red dyestuff (having an SAC which peaks at about 500 nanometers) used as the masking dyestuff should be present in the impregnating solution at a concentration of about from 0.15 mg/ml to 0.35 mg/ml. Other chromogenic materials reactable with ethylene and propylene glycol in coolants are tetrabromophenol-phthalein ethyl ester, bromphenol blue, bromcresol green, methyl yellow and bromcresol purple. These materials are commonly known as protein error indicators.

In addition to the chromogenic material used in the ethylene or propylene glycol freezepoint coolant test, it is necessary that a buffer be utilized to maintain the pH of the test system within the normal color change pH range of the chromogenic materials. The usual buffers known to those skilled in the art of formulating such test devices may be employed.

The present invention will be more fully described in the following examples:

EXAMPLE 1

Using a Standard Test Device for the Determination of Ethylene and Propylene Glycol in Standard and Longlife Coolants Reagent strips were prepared by first preparing a mixture of the following A and B formulations:

| A. Reagent ethyl alcohol | 0.318 | liters |
|---|---|---|
| Tetrabromphenol blue | 0.267 | grams |
| B. Distilled water | 0.68 | liters |
| Sodium citrate | 48.0 | grams |
| Citric acid | 104.5 | grams |
| Sodium chloride | 4.60 | grams | dipping Ahlstrom 204 paper into the mixture and drying at 220 degrees F. for approximately 4 minutes. The paper was cut into ⅕ inch squares and the squares attached to the end portion of strips of semirigid polystyrene ⅕ inch wide by about 3 inches long using double faced plastic adhesive tape. The resulting strips were stored in tightly sealed bottles with sufficient desiccant to keep the test devices dry. A standard color chart had previously been prepared by dipping the reagent strips into a series of known concentrations of ethylene glycol and matching the color developed in about 15 seconds against color chips from standard books of color.

The strips were then contacted with samples of 1) standard green colored radiator coolant and 2) Texaco Longlife Coolant, Part No. CAT EC-1, having an intense red coloration, the samples having varying concentrations of ethylene glycol, and read by an experienced test strip reader using the developed color charts. The color matches between the reacted strips and the color blocks with the standard green colored coolant were excellent whereas use of the strips with the Texaco samples produced varying shades of gray which did not match any of the color blocks and accordingly were not usable.

The strips reacting with each of the samples having 32–33% ethylene glycol concentrations were then examined on a Macbeth Color-Eye Model 1500 PLUS reflectance measuring device and curves were generated as shown in FIG. 1.

EXAMPLE 2

Use of a Red Masking Dyestuff in Test Strip

The testing regime described in Example 1 was repeated except that a test strip containing a red masking dyestuff was used which was prepared by adding 0.294 grams of F D & C Red No. 40 to the part B. of the formula described in Example 1. All other parameters of the formulation and process of making the test strips remained the same except that a new color chart was prepared based on the addition of the red masking dyestuff to the formulation.

Figure 2:
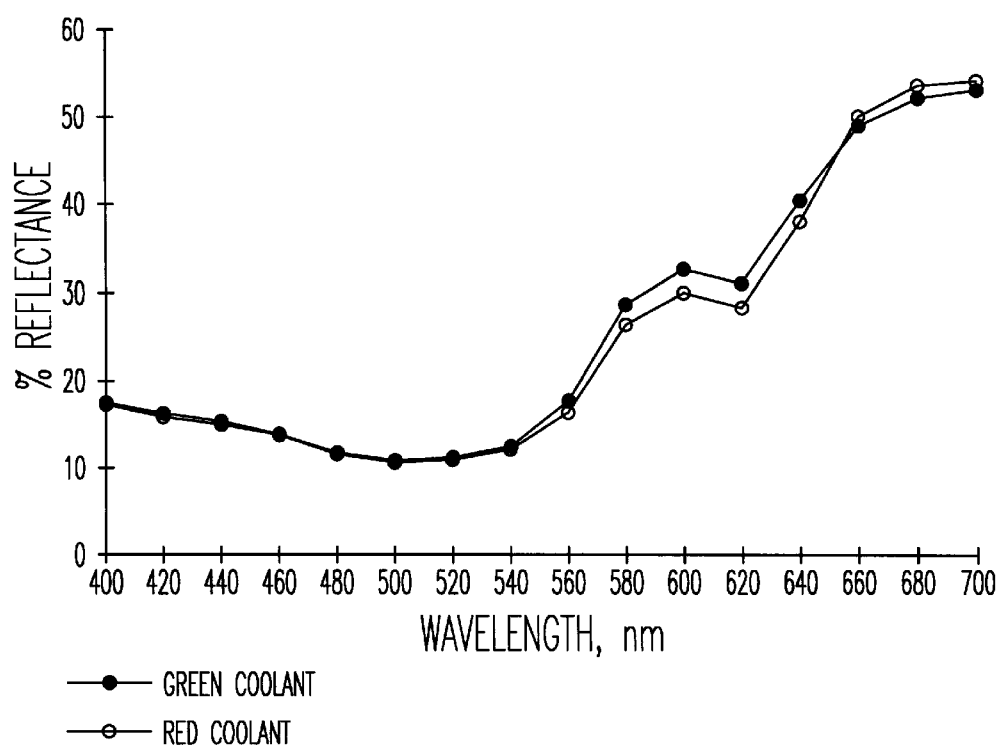
FIG. 2 is a graph showing spectral percent reflectance curves representing the results of Example 2 wherein red and green colored coolants are tested for the presence and amount of ethylene glycol using the composition of Example 1 except that F D & C Red No. 40 dyestuff is added to the reagent composition.

Comparable good to excellent results were obtained with both the green and red colored coolant samples. SRCs were likewise developed using the Macbeth reflectance device described above, the curves shown in FIG. 2.

EXAMPLE 3

Use of Red Masking Dyestuff in Test Strips Contacted with Blue Colored Coolant

Figure 3:
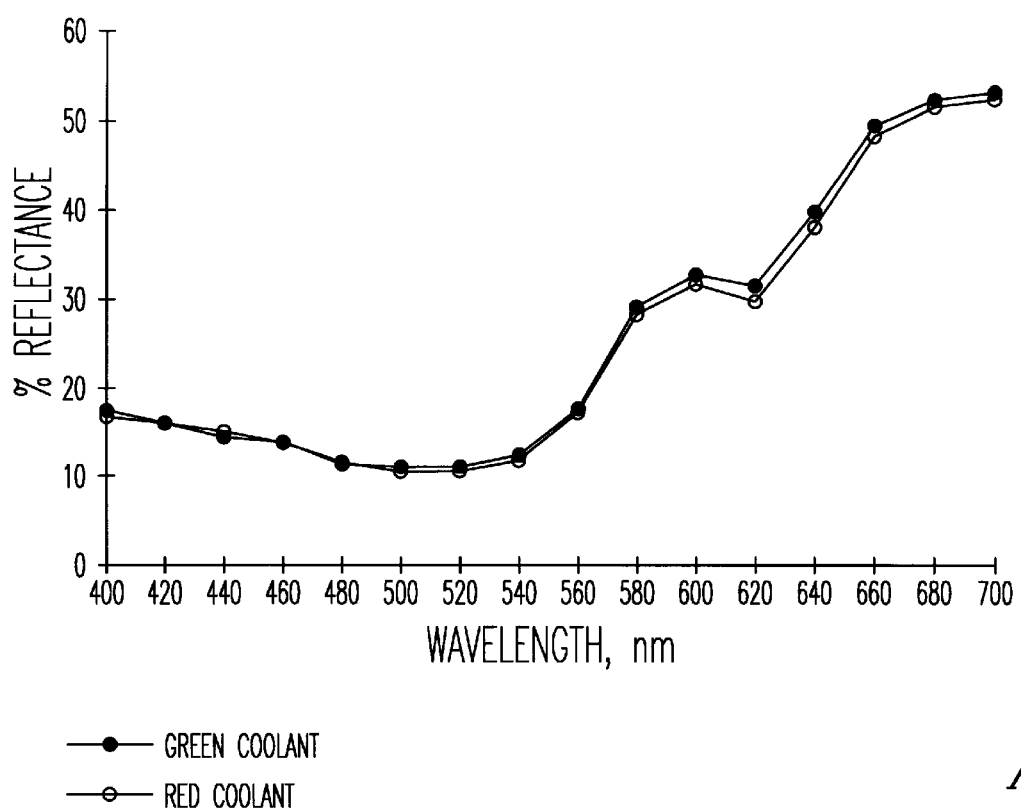
FIG. 3 is a graph showing spectral percent reflectance curves representing the results of Example 3 wherein blue and green colored coolants are tested for the presence and amount of propylene and ethylene glycol respectively, using the composition of Example 1 except that F D & C Red No. 40 is added to the reagent composition.

Example 2 was repeated except that results were obtained on test strips contacting coolant samples having green and blue interfering colors. Comparable good results were obtained and SRCs developed using the reflectance instrument described in Example 1. FIG. 3 shows such results for 32–33% ethylene (green) and propylene (blue) glycol sample solutions.

What is claimed is:

1. A method for colorimetrically determining an analyte in a liquid test sample which sample additionally contains one or more interfering colored substances, said solution of analyte and interfering colored substances having certain color characteristics, the method comprising:

A. contacting the solution containing the interfering colored substance with a test device comprising a porous matrix incorporated with a test reagent composition containing a chromogenic material specifically reactable with said analyte to generate a visual colorimetric response thereto, said matrix additionally containing a masking dyestuff having essentially the same color characteristics as the interfering material and having color characteristics which when combined with the color generated by the chromogenic material and the interfering colored substance results in the appearance of a color having characteristics which are changed from the interfering color, said masking dyestuff being present in an amount effective to accomplish said change permitting the visual estimation of the response of the chromogenic material to the presence of the analyte in the test fluid sample; and, B. comparing and correlating the color developed in the matrix by the test composition to a series of known standard solutions of analyte to give a quantitative result of the amount of analyte in the test sample fluid.

2. The method of claim 1 wherein the analyte is selected from the group consisting of ethylene and propylene glycol and the chromogenic indicator material is a protein error indicator.

3. The method of claim 2 wherein the protein error indicator is tetrabromophenol blue.

4. The method of claim 2 wherein the masking dyestuff is a red colored material.

5. The method of claim 4 wherein the masking dyestuff has a spectral absorbance curve which peaks at about from 450 to 600 nm.

6. The method of claim 4 wherein the masking dyestuff is Food Drug and Cosmetic Red No. 40.

7. A test device for colorimetrically determining an analyte in a liquid test sample which sample additionally contains one or more interfering colored substances, said solution of analyte and interfering colored substances having certain color characteristics, the device comprising a porous matrix incorporated with a test reagent composition containing a chromogenic indicator material specifically reactable with said analyte to give a visual colorimetric response thereto, said matrix additionally containing a masking dyestuff having essentially the same color characteristics as the interfering material and having color characteristics which when combined with the color generated by the chromogenic indicator material reacting with the analyte and interfering colored substance changes the total visual color response spectrum which allows a visual determination of the color response of the chromogen reacting with the analyte present in the test sample, said masking dyestuff being present in an amount effective to suppress the interference due to the colored material in the test fluid sample and allowing a visual estimation of the color of the chromogenic materials proportionally responding to the presence of the analyte in the test fluid sample.

8. A test device as in claim 7 wherein the chromogenic material is a protein error indicator.

9. A test device as in claim 8 wherein the protein error indicator is tetrabromophenol blue.

10. A test device as in claim 9 wherein the masking dyestuff is red material.

11. A test device as in claim 10 wherein the masking dyestuff has a spectral absorbance curve which peaks at about from 450 to 600 nm.

12. A test device as in claim 11 wherein the spectral absorbance curve peaks at about 500 nm.

13. A test device as in claim 11 wherein the masking dyestuff is Food Drug and Cosmetic red No. 40.

14. A test device as in claim 8 wherein the porous matrix is absorbent paper.

15. A method for calorimetrically determining an analyte in a liquid test sample which contains one or more interfering colored substances, said method comprising:

A. contacting the solution containing the interfering colored substance with a test device comprising a porous matrix incorporated with a test reagent composition containing a chromogenic material specifically reactable with said analyte to generate a visual calorimetric response thereto, said matrix additionally containing essentially a masking dyestuff having red spectro color characteristics which, when combined with the color generated by the chromogenic material and the interfering colored substance, results in the appearance of a color having characteristics which are changed from the interfering color, said red masking dyestuff being present in an amount effective to accomplish said change permitting the visual estimation of the response of the chromogenic material to the presence of the analyte in the test fluid sample; and B. comparing and correlating the color developed in the matrix by the test composition to a series of known standard solutions of analyte to give a quantitative result of the amount of analyte in the test fluid.

16. The method of claim 15 wherein the liquid test sample is a vehicular fluid.

17. The method of claim 16 wherein the vehicular fluid is a coolant.

* * * * *